(12) United States Patent
Inoue et al.

(10) Patent No.: US 10,660,738 B2
(45) Date of Patent: May 26, 2020

(54) ENDOVASCULAR TREATMENT ASSISTANCE TOOL

(71) Applicants: Toray Industries, Inc., Tokyo (JP); Kanji Inoue, Kyoto-shi (JP)

(72) Inventors: Kanji Inoue, Kyoto (JP); Takahiro Yagi, Otsu (JP); Masaki Fujita, Otsu (JP); Koji Kadowaki, Otsu (JP); Kazuhiro Tanahashi, Otsu (JP)

(73) Assignees: Toray Industries, Inc., Tokyo (JP); Kanji Inoue, Kyoto-shi (JP)

( * ) Notice: Subject to any disclaimer, the term of this patent is extended or adjusted under 35 U.S.C. 154(b) by 277 days.

(21) Appl. No.: 15/306,505

(22) PCT Filed: May 8, 2015

(86) PCT No.: PCT/JP2015/063265
§ 371 (c)(1),
(2) Date: Oct. 25, 2016

(87) PCT Pub. No.: WO2015/170732
PCT Pub. Date: Nov. 12, 2015

(65) Prior Publication Data
US 2017/0049552 A1 Feb. 23, 2017

(30) Foreign Application Priority Data

May 9, 2014 (JP) ................................ 2014-097539
Jul. 30, 2014 (JP) ................................ 2014-154888

(51) Int. Cl.
*A61F 2/01* (2006.01)
*A61L 33/00* (2006.01)
*A61B 17/00* (2006.01)

(52) U.S. Cl.
CPC .............. *A61F 2/013* (2013.01); *A61B 17/00* (2013.01); *A61L 33/0035* (2013.01);
(Continued)

(58) Field of Classification Search
CPC ...... A61F 2/01; A61F 2/013; A61F 2002/015; A61F 2002/016; A61F 2002/011; A61F 2002/018; A61B 17/00
See application file for complete search history.

(56) References Cited

U.S. PATENT DOCUMENTS 6,152,946 A * 11/2000 Broome .................... A61F 2/01
606/200
2001/0041908 A1 11/2001 Levinson et al.
(Continued)

FOREIGN PATENT DOCUMENTS

CN 103596603 2/2014
EP 1 020 495 7/2000
(Continued)

OTHER PUBLICATIONS

Supplementary Search Report dated Mar. 6, 2018, of counterpart European Application No. 15788802.5.

*Primary Examiner* — Kathleen S Holwerda
*Assistant Examiner* — Kankindi Rwego
(74) *Attorney, Agent, or Firm* — DLA Piper LLP (US)

(57) ABSTRACT

A treatment aiding device includes a flexible shaft; a filter; linear supporting members; an elastomer member composed of an elastomer in which a penetrating hole is formed, which elastomer member is arranged in the proximal side relative to the opening section of the filter such that the shaft penetrates the penetrating hole, wherein the outer diameter of the end face in which the penetrating hole is formed is larger than the outer diameter of the opening-section side of the filter when the filter is closed; and an outer tube in which a penetrating hole is formed, which outer tube is arranged in the proximal side relative to the opening section of the filter such that the shaft penetrates the penetrating hole in a state which allows movement of the shaft in the longitudinal direction; wherein the elastomer member is fixed in the distal side of the outer tube.

11 Claims, 4 Drawing Sheets

(52) U.S. Cl.
CPC ... *A61F 2002/011* (2013.01); *A61F 2002/015* (2013.01); *A61F 2002/016* (2013.01); *A61F 2230/0067* (2013.01); *A61F 2230/0069* (2013.01); *A61F 2230/0093* (2013.01)

(56) References Cited

U.S. PATENT DOCUMENTS

| | | | |
|---|---|---|---|
| 2004/0158275 A1 | 8/2004 | Crank et al. | |
| 2004/0167564 A1 | 8/2004 | Fedie | |
| 2004/0167566 A1 | 8/2004 | Beulke et al. | |
| 2004/0243173 A1 | 12/2004 | Inoue | |
| 2005/0159773 A1* | 7/2005 | Broome | A61F 2/013 606/200 |
| 2008/0033483 A1* | 2/2008 | Isshiki | A61F 2/013 606/200 |
| 2008/0045999 A1 | 2/2008 | Tsugita et al. | |
| 2012/0231043 A1 | 9/2012 | Leontein et al. | |
| 2016/0296679 A1* | 10/2016 | Kadowaki | A61L 33/0076 |

FOREIGN PATENT DOCUMENTS

| | | |
|---|---|---|
| JP | 2003-505216 A | 2/2003 |
| JP | 2008-035923 A | 2/2008 |
| JP | 4073869 B2 | 4/2008 |
| WO | 03/084437 A2 | 10/2003 |
| WO | 2008/005898 A2 | 1/2008 |
| WO | 2012/176841 A2 | 12/2012 |
| WO | 2013/059069 A2 | 4/2013 |

\* cited by examiner

ENDOVASCULAR TREATMENT ASSISTANCE TOOL

TECHNICAL FIELD

This disclosure relates to the field of medical instruments, and relates to, in particular, an endovascular treatment aiding device that captures free thrombi or the like during percutaneous treatment for a blood vessel.

BACKGROUND

In recent years, the number of patients with cardiac infarction, cerebral infarction or the like is increasing. These infarctions are caused by interruption of blood flow due to obstruction or stenosis of a blood vessel, which occurs by deposition of thrombi, plaques or the like on the vascular wall. In general, for treatment of a site of obstruction or stenosis in a blood vessel, percutaneous treatment by balloon angioplasty or stenting using a balloon catheter or a stent is carried out.

In treatment by balloon angioplasty, an inflatable balloon at the distal end portion of a balloon catheter is expanded at a site of obstruction or stenosis in a blood vessel to secure the intravascular lumen and to thereby maintain the blood flow. However, when a blood vessel is expanded by the balloon, thrombi or plaques deposited on the vascular wall might be unexpectedly released, and such a substance might then be carried away by blood flow to cause obstruction of a peripheral thin blood vessel, resulting in infarction.

In treatment by stenting, a stent composed of a material such as nitinol or cobalt alloy having the shape of an almost cylindrical tube or mesh sleeve is permanently or temporarily introduced to a site of stenosis in a blood vessel to secure the intravascular lumen and to thereby maintain blood flow. However, similar to balloon angioplasty, when the stent is placed in a blood vessel, thrombi or plaques deposited on the vascular wall might be unexpectedly released, causing infarction.

An endovascular treatment aiding device to be used in combination with a treatment device such as a balloon catheter or a stent has been developed to avoid such a risk. The endovascular treatment aiding device is percutaneously placed in a site which is more peripheral than the lesion where the balloon catheter or the stent is to be placed, and used to capture thrombi or plaques released from the vascular wall.

As such an endovascular treatment aiding device, one having a structure containing: a shaft with an outer diameter which allows the shaft to pass through the guide wire lumen of a treatment device such as a balloon catheter; and a filter fixed in the distal side of the shaft has been reported. The filter has a mesh-shaped or sheet-shaped membrane composed of a polymer material on which a plurality of openings are formed, and has a shape in which the peripheral vessel side, that is, the distal side, is closed, and the central vessel side, that is, the proximal side, is open (JP 2008-35923 A).

By this, during treatment using a treatment device such as a balloon catheter, thrombi or plaques released and carried away from the vascular wall can be captured by the filter constituting a part of the endovascular treatment aiding device placed in the peripheral side without blocking blood flow.

When such an endovascular treatment aiding device is used, the endovascular treatment aiding device, with its filter closed, is contained in a delivery sheath and delivered to the site where the device is to be placed, which is located more peripheral than the lesion. After delivery, the filter is released by removal of the delivery sheath to the outside of the body. This causes self-expansion of the opening section of the filter, thereby allowing close contact of the opening section to the vascular wall. When the endovascular treatment aiding device is to be retrieved, a retrieval sheath is delivered along the endovascular treatment aiding device, and the filter containing thrombi or plaques is stored inside the retrieval sheath, followed by its removal to the outside of the body.

As an endovascular treatment aiding device that enables reduction of leakage of thrombi, plaques or the like by increasing adhesion to the vascular wall, an endovascular treatment aiding device comprising a ring-shaped member formed with a superelastic metal provided in the opening section of the filter, wherein, by folding the ring-shaped member by bundling of a supporting member that acts as a support between the shaft and the ring-shaped member, the filter can be folded into a bag shape, has been reported (JP 4073869 B).

When such an endovascular treatment aiding device is placed in a blood vessel, the living body recognizes it as a foreign substance, and blood coagulation reaction proceeds to cause formation of a thrombus. Therefore, antithrombogenicity is required for the device. In view of this, endovascular treatment aiding devices to which antithrombogenic compounds are given have been reported (WO 2003/084437, WO 2008/005898 and WO 2013/059069).

However, in the endovascular treatment aiding device described in JP '923, contacting with the stent may occur during delivery of a retrieval sheath because of the thick diameter of the distal end of the retrieval sheath so that there is a possibility that the retrieval sheath cannot be delivered to the filter. Moreover, since the opening section of the filter does not have a ring shape, its adhesion to the vascular wall is insufficient so that there is a possibility of leakage of thrombi, plaques, or the like during treatment using a balloon catheter or the like.

In the endovascular treatment aiding device described in JP '869, a sudden diameter transition like step is generated between the opening section of the filter and the shaft when the filter is in the closed state. Therefore, when the endovascular treatment aiding device is used at the same time as a treatment device such as a balloon catheter or a stent, there is a possibility that the end portion of the stent or the distal end portion of the guiding catheter is caught in the step generated between the opening section of the filter and the shaft, and a part of the filter is turned up, leading to leakage of the thrombi or the plaques captured.

Although WO '437, WO '898 and WO '069 describe giving of antithrombogenic compounds to endovascular treatment aiding devices, there is no description on the optimal types and combinations of the antithrombogenic compounds.

That is, conventionally, there is no known endovascular treatment aiding device that solves both of the two problems, that is, there is no known endovascular treatment aiding device that, during its retrieval, securely allows delivery of a retrieval sheath to the filter, and can prevent the filter with captured thrombi or plaques from being caught in a device such as a stent or a guiding catheter.

It could therefore be helpful to provide an endovascular treatment aiding device that, during its retrieval, securely allows delivery of a retrieval sheath to the filter, and can prevent the filter with captured plaques or the like from being caught in a treatment device such as a stent or a guiding catheter.

SUMMARY

We thus provide (1) to (12):

(1) An endovascular treatment aiding device comprising:
a flexible shaft;
a filter fixed to the shaft such that a closed-end section is formed in the distal side in the longitudinal direction of the shaft, and an opening section is formed in the proximal side in the longitudinal direction, which filter can be opened and closed in an umbrella-like manner;
a supporting member composed of linear members each of which is fixed to the end portion in the opening-section side of the filter and a part of the shaft such that these are connected to each other, which linear members enable to close the filter by tension caused by application of an external force to the proximal side in the longitudinal direction; and
an elastomer member which is a member composed of an elastomer in which a penetrating hole (A) is formed, the elastomer member being arranged in the proximal side in the longitudinal direction relative to the opening section of the filter such that the shaft penetrates the penetrating hole (A), wherein the outer diameter of the end face in which the penetrating hole (A) is formed is larger than the outer diameter of the opening-section side of the filter when the filter is closed; and comprising:
an outer tube in which a penetrating hole (B) is formed, the outer tube being arranged in the proximal side in the longitudinal direction relative to the opening section of the filter such that the shaft penetrates the penetrating hole (B) in a state which allows movement of the shaft in the longitudinal direction;
wherein the elastomer member is fixed in the distal side in the longitudinal direction of the outer tube.

(2) The endovascular treatment aiding device according to (1), further comprising an annular member in which a penetrating hole Ⓒ is formed, the annular member being arranged in the proximal side in the longitudinal direction relative to the opening section of the filter such that the shaft penetrates the penetrating hole Ⓒ in a state which allows movement of the shaft in the longitudinal direction, the annular member having a thick section whose outer diameter is smaller than the outer diameter of the opening-section side of the filter when the filter is closed, and whose outer diameter is larger than the inner diameter of the elastomer member.

(3) The endovascular treatment aiding device according to (1) or (2), wherein, when the outer tube is slid toward the distal side in the longitudinal direction, the filter is closed by bundling of the supporting member.

(4) The endovascular treatment aiding device according to any one of (1) to (3), wherein, when the outer tube is slid toward the distal side in the longitudinal direction to close the filter, the endovascular treatment aiding device can have a shape in which the elastomer member covers the thick section, and the thick section is pressed into the penetrating hole (A).

(5) The endovascular treatment aiding device according to any one of (1) to (4), which can be contained in a sheath when the filter is in a closed state.

(6) The endovascular treatment aiding device according to any one of (1) to (5), wherein a cationic polymer containing, as constituent monomers, at least one compound selected from the group consisting of alkyleneimine, vinylamine, allylamine, lysine, protamine, and diallyldimethylammonium chloride is covalently bound to the filter, and an anionic sulfur compound having anticoagulant activity is bound to the filter and/or the cationic polymer.

(7) The endovascular treatment aiding device according to any one of (1) to (6), wherein the ratio of the abundance of nitrogen atoms to the abundance of total atoms on the surface of the filter as measured by X-ray photoelectron spectroscopy (XPS) is 7.0 to 12.0 atomic percent.

(8) The endovascular treatment aiding device according to any one of (1) to (7), wherein the ratio of the abundance of sulfur atoms to the abundance of total atoms on the surface of the filter as measured by X-ray photoelectron spectroscopy (XPS) is 3.0 to 6.0 atomic percent.

(9) The endovascular treatment aiding device according to any one of (1) to (8), wherein the anionic sulfur compound having anticoagulant activity is at least one selected from the group consisting of heparin and heparin derivatives.

(10) The endovascular treatment aiding device according to any one of (1) to (9), wherein the surface amount of the anionic sulfur compound having anticoagulant activity on the filter after soaking in physiological saline at 37° C. for 30 minutes as measured based on the anti-factor Xa activity is not less than 30 mIU/cm$^2$.

(11) The endovascular treatment aiding device according to any one of (1) to (10), wherein the cationic polymer and the anionic sulfur compound having anticoagulant activity form an antithrombogenic compound layer with a thickness of 1 to 600 nm on the surface of the filter.

(12) The endovascular treatment aiding device according to any one of (1) to (11), wherein the filter is formed with polyester.

We provide an endovascular treatment aiding device wherein, since the outer diameter of the distal side in the longitudinal direction of the elastomer member is larger than the outer diameter of the opening section of the filter when the filter is closed, the step present between the opening section of the filter and the shaft can be covered so that the endovascular treatment aiding device can be prevented from being caught in a device such as a stent or a guiding catheter during its retrieval.

DESCRIPTION OF SYMBOLS

Figure 1:
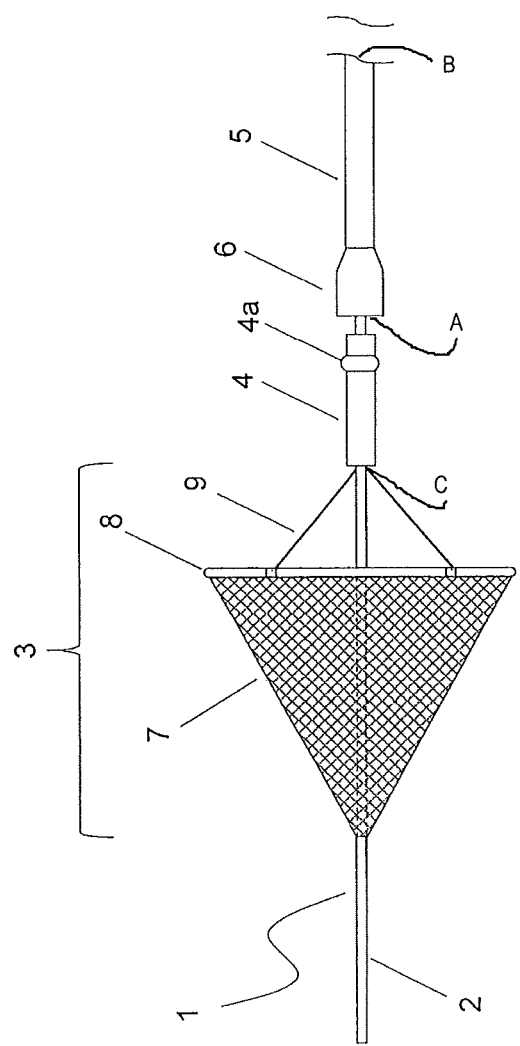
FIG. 1 is a schematic view showing a side view, in the longitudinal direction, of the endovascular treatment aiding device according to an example.

1 Endovascular treatment aiding device
2 Shaft
3 Filter section
4 Annular member
5 Outer tube
6 Elastomer member
7 Filter section
8 Ring
9 Supporting member
10 Endovascular treatment aiding device
11 Annular member

DETAILED DESCRIPTION

Our endovascular treatment aiding device comprises:
a flexible shaft;
a filter fixed to the shaft such that a closed-end section is formed in the distal side in the longitudinal direction of the shaft, and an opening section is formed in the proximal side in the longitudinal direction, which filter can be opened and closed in an umbrella-like manner;
a supporting member composed of linear members each of which is fixed to the end portion in the opening-section side of the filter and a part of the shaft such that these are connected to each other, which linear members enable to close the filter by tension caused by application of an external force to the proximal side in the longitudinal direction; and
an elastomer member which is a member composed of an elastomer in which a penetrating hole (A) is formed, the elastomer member being arranged in the proximal side in the longitudinal direction relative to the opening section of the filter such that the shaft penetrates the penetrating hole (A), wherein the outer diameter of the end face in which the penetrating hole (A) is formed is larger than the outer diameter of the opening-section side of the filter when the filter is closed;
and comprises:
an outer tube in which a penetrating hole (B) is formed, the outer tube being arranged in the proximal side in the longitudinal direction relative to the opening section of the filter such that the shaft penetrates the penetrating hole (B) in a state which allows movement of the shaft in the longitudinal direction;
wherein the elastomer member is fixed in the distal side in the longitudinal direction of the outer tube.

Specific examples are described below with reference to the drawings. However, this disclosure is not limited to the examples. Each identical element is represented using an identical symbol and redundant explanations are omitted. The ratios used in the drawings are not necessarily the same as those in the description. The following terms used in the description are defined as described below unless otherwise specified.

FIG. 1 is a schematic view showing a side view, in the longitudinal direction, of the endovascular treatment aiding device 1 according to an example. The endovascular treatment aiding device 1 shown in FIG. 1 can pass through the inside of a guide wire lumen of a treatment device such as a balloon catheter, and comprises: a linear shaft 2 having flexibility; a filter section 3 which can capture thrombi, plaques or the like; an annular member 4 having a thick section 4a; an outer tube 5 arranged in the proximal side in the longitudinal direction relative to the annular member 4; and an elastomer member 6.

The shaft 2 preferably has flexibility to achieve secure delivery to the peripheral side relative to the lesion where the treatment device is to be placed. The term "having flexibility" means that the original shape of the shaft can be recovered after bending the shaft at an angle of 180° such that the radius of curvature is 100D, wherein D represents the diameter of the shaft.

The filter section 3 comprises: a filter 7 in which a plurality of openings are formed, which filter 7 is arranged in the distal side in the longitudinal direction of the shaft 2, and can be opened and closed in an umbrella-like manner; a ring 8 having a circular shape which is provided in the proximal side in the longitudinal direction of the filter 7, that is, the opening-section side of the filter 7, which ring 8 is composed of a flexible wire having elastic restoring force; and a supporting member 9 composed of linear members arranged between the shaft 2, and the filter 7 and the ring 8 such that the filter 7 can be closed by tension caused by application of an external force to the proximal side in the longitudinal direction. The distance between the distal side in the longitudinal direction of the filter 7 and the distal side of the shaft 2 is preferably 5 to 20 mm, more preferably 10 to 15 mm. The distance between the distal side in the longitudinal direction of the balloon portion of the balloon catheter and the proximal side in the longitudinal direction of the filter 7 is preferably not more than 10 mm.

The distal side in the longitudinal direction means the peripheral side of the blood vessel, and the proximal side in the longitudinal direction means the central side of the blood vessel.

The annular member 4, in which a thick section 4a and a penetrating hole (C) are formed, is movably arranged on the shaft 2 so that it can be arranged at a position where it contacts the proximal side in the longitudinal direction of the filter section 3 when the filter section 3 is closed. The annular member 4 can therefore be slid on the shaft 2.

The thick section 4a is a portion on the annular member 4 where the diameter in the direction vertical to the longitudinal direction is locally increased. The thick section 4a is preferably a portion where the outer diameter is smaller than the outer diameter of the opening-section side of the filter section 3 when the filter section 3 is closed, and the outer diameter is larger than the inner diameter of the elastomer member 6.

The outer tube 5, in which a penetrating hole (B) is formed, is movably arranged on the shaft 2. It can therefore slide on the shaft 2. To improve kink resistance of the shaft 2, and securing rigidity required to close the filter section 3, a braided layer using a metal wire such as a stainless steel wire or using a resin such as a polyamide may be incorporated in the outer tube 5.

The elastomer member 6, in which a penetrating hole (A) is formed, is movably arranged on the shaft 2 in the proximal side in the longitudinal direction relative to the opening section of the filter section 3. The elastomer member 6 can therefore slide on the shaft 2. During operation, to adjust the position of placement of the endovascular treatment aiding device 1 in the blood vessel, the outer tube 5 in the operator side, where the operator manipulates the device, may be slid toward the distal side or the proximal side in the longitudinal direction. Thus, the proximal end portion in the longitudinal direction of the elastomer member 6 is preferably fixed to the distal end portion in the longitudinal direction of the outer tube 5 since, without the fixation, the elastomer member 6 may not follow the sliding of the outer tube 5 and, therefore, adjustment of the relative positions of the elastomer member 6 and the filter section 3 may be impossible.

The filter 7 is fixed to the shaft 2 such that the distal side in the longitudinal direction of the filter 7 is closed. This portion of fixation is provided as the closed-end section. The proximal side in the longitudinal direction of the filter 7 is open. This portion of opening is provided as the opening section. To increase adhesion to the vascular wall, the opening section of the filter 7 is preferably fixed to the entire circumference of the ring 8 having a circular shape so that the filter 7 can be opened and closed by movement of the ring 8.

The supporting member 9 is constituted of a plurality of linear members. In the end portion of the opening-section side of the filter 7, each linear member is fixed to the filter 7 and the ring 8 and, on the shaft 2, the linear members are fixed together to the same position, thereby connecting the filter 7 and the ring 8 to the part of the shaft 2. In the example shown in FIG. 1, the supporting member 9 is constituted of a plurality of linear members. The number of the linear members in the supporting member 9, and the positions in the filter 7 and the ring 8 to which the linear members are fixed, are not limited. The linear members may be in a number with which the filter 7 and the ring 8 can be closed by the supporting member 9. The position where the supporting member 9 is fixed on the shaft 2 is also not limited. The position is preferably in the proximal side in the longitudinal direction relative to the opening section of the filter section 3.

To cover the step formed between the opening section of the filter section 3 and the shaft 2, and to thereby prevent the endovascular treatment aiding device 1 from being caught in a device such as a stent or a guiding catheter during retrieval, the end face in the distal side in the longitudinal direction of the penetrating hole (A) formed in the elastomer member 6 is designed such that its outer diameter can become larger than the outer diameter of the opening-section side of the filter section 3 when its opening section is closed. If the elastomer member 6 after the change in the outer diameter (expansion) has over-covered the filter section 3 in the closed state, the outer diameter of the endovascular treatment aiding device 1 becomes large, leading to difficulty in the retrieval using a retrieval sheath. Thus, the inner diameter of the end face in the distal side in the longitudinal direction of the penetrating hole (A) formed in the elastomer member 6, after the change in the outer diameter, is preferably smaller than the outer diameter of the opening-section side of the filter section 3 when its opening section is closed. The elastomer member 6 after the change in the outer diameter (expansion) preferably contains a taper section in which the outer diameter decreases toward the proximal side in the longitudinal direction of the shaft 2, from the viewpoint of preventing the member from being caught in a treatment device.

Figure 2:
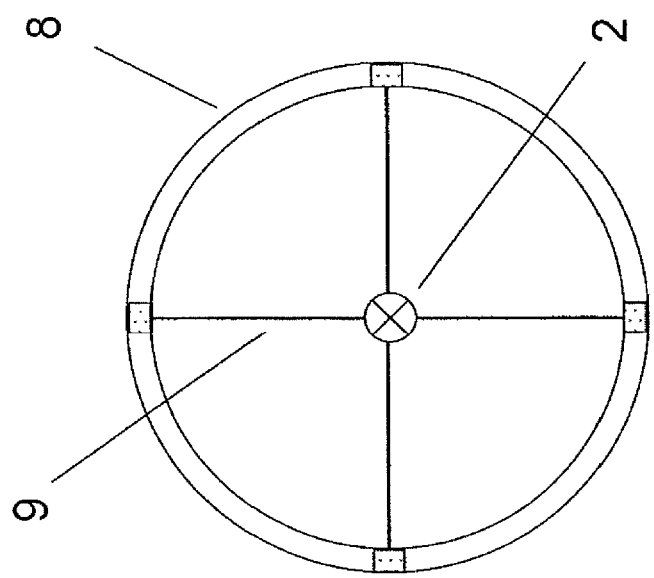
FIG. 2 is a schematic view showing a front view, in the longitudinal direction, of the endovascular treatment aiding device according to an example, wherein the positional relationships among the filter, the ring, and the supporting member in the filter section are illustrated.

FIG. 2 is a schematic view showing a front view, in the longitudinal direction, of the endovascular treatment aiding device 1 according to an example, wherein the positional relationships among the ring 8 and the supporting member 9 in the filter section 3, and the shaft 2, are illustrated. As shown in FIG. 2, the supporting member 9 is fixed to the ring 8 such that the circumference of the ring 8 is equally divided at four points. By making the supporting member 9 have a uniform length, the shaft 2 is in a state where it is positioned on the central axis of the ring 8.

Figure 3:
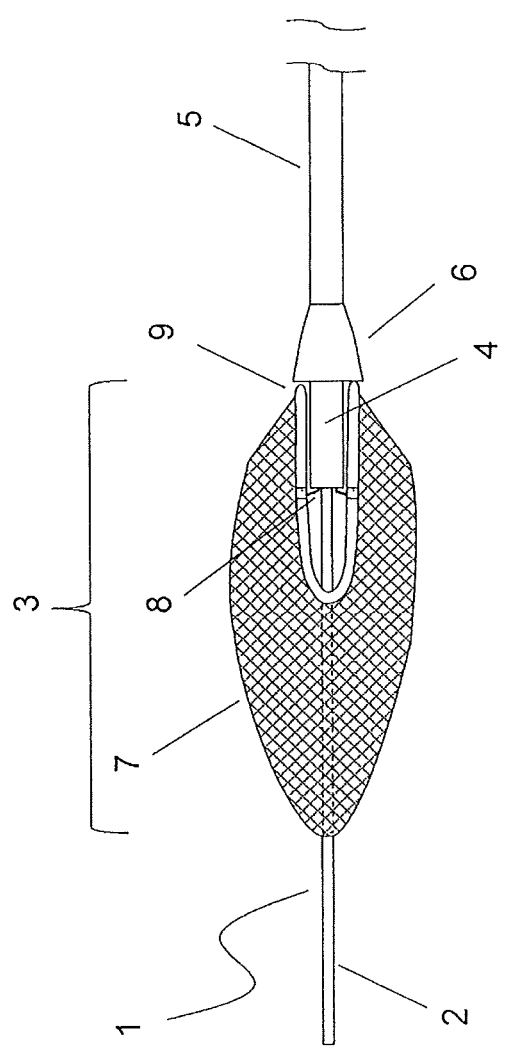
FIG. 3 is a schematic view showing a side view, in the longitudinal direction, of the endovascular treatment aiding device according to an example, wherein the opening section of the filter section is closed.

FIG. 3 is a schematic view showing a side view, in the longitudinal direction, of the endovascular treatment aiding device 1 according to an example, wherein the opening-section of filter section 3 is closed. The inner diameter of the distal side in the longitudinal direction of the penetrating hole (A) formed in the ring-shaped elastomer member 6 is smaller than the outer diameter of the thick section 4a present in the proximal side in the longitudinal direction of the penetrating hole (C) formed in the annular member 4. Therefore, by sliding the elastomer member 6, or the outer tube 5 to which the elastomer member 6 is fixed, toward the distal side in the longitudinal direction on the shaft 2, the annular member 4 can be slid toward the distal side in the longitudinal direction on the shaft 2. The penetrating hole (B) formed in the outer tube 5, and the penetrating hole (C) formed in the annular member 4, have inner diameters which allow the linear supporting member 9 to pass therethrough. Therefore, when an external force is applied to the proximal side in the longitudinal direction of the supporting member 9 to cause tension, the supporting member 9 is drawn, while being bundled, into the gap between each penetrating hole and the shaft 2, as the supporting member 9 slides on the shaft 2. When the distal end portion in the longitudinal direction of the annular member 4 reaches the position where the drawing of the supporting member 9 has proceeded to the end portion in the opening-section side of the filter section 3, that is, when the annular member 4 finishes bundling of the supporting member 9, the opening section of the filter section 3 becomes a closed state. At this time, the filter section 3 is not in close contact with the shaft 2 so that a step is formed between the opening section of the filter section 3 and the shaft 2.

In this state, when the operator further attempts to slide the elastomer member 6, or the outer tube 5 to which the elastomer member 6 is fixed, toward the distal side in the longitudinal direction on the shaft 2, the annular member 4 is prevented from further sliding toward the distal side by the presence of the filter section 3 containing the completely bundled supporting member 9 and, as a result, the distal end portion in the longitudinal direction of the flexible elastomer member 6 covers the thick section 4a present in the proximal side in the longitudinal direction of the annular member 4 so that the thick section 4a is pressed into the penetrating hole (A) formed in the elastomer member 6. When the elastomer member covers the thick section 4a, the outer diameter of the end face of the penetrating hole (A) formed in the elastomer member 6 becomes larger than the outer diameter of the opening section of the filter section 3 when its opening section is closed. Since, by this, the step formed between the opening section of the filter section 3 and the shaft 2 can be covered, the endovascular treatment aiding device 1 can be prevented from being caught in a treatment device such as a stent or a guiding catheter during retrieval. The inner diameter of the end face in the distal side in the longitudinal direction of the penetrating hole (A) formed in the elastomer member 6 covering the thick section 4a is preferably smaller than the outer diameter of the opening section of the filter section 3 when its opening section is closed. In this case, the step formed between the opening section of the filter section 3 and the shaft 2 can be more securely covered.

The material of the shaft 2, which acts as the core member of the endovascular treatment aiding device 1, is preferably a metal commonly used for guide wires such as a stainless steel, tungsten, or cobalt alloy.

Examples of the material of the annular member 4 include metals such as stainless steels, platinum alloys, and palladium alloys. From the viewpoint of simplicity in production, the material of the annular member 4 is more preferably a resin such as a polycarbonate, polypropylene, or polyethylene that can be molded using a mold or the like.

The material of the outer tube 5 is not limited as long as it can achieve both rigidity required to close the filter section 3 by tension caused by bundling of the supporting member 9 by the annular member 4, and flexibility required to secure the blood vessel tracking ability. Examples of the material of the outer tube 5 include metals such as nickel alloys and stainless steels. The material of the outer tube 5 is more preferably a resin such as a polyimide or polyamide.

When the material of the outer tube 5 is a resin such as a polyimide or polyamide, an easily slidable resin such as a polyimide, polyamide, or polyethylene blended with a polytetrafluoroethylene, tetrafluoroethylene copolymer, and/or lubricant may be incorporated into an inner layer to increase slidability of the outer tube 5 on the shaft 2. To secure the rigidity required to close the filter section 3, a braided layer prepared using a metal wire such as a stainless steel wire or using a resin such as a polyamide may also be incorporated.

The outer tube 5 may also have a function as a sheath. When the outer diameter of the outer tube 5 is one with which the whole outer tube 5 can be contained in a treatment device such as a balloon catheter, and the inner diameter of the penetrating hole (B) is one with which the whole filter section 3 with its opening section closed can be contained in the penetrating hole (B), the endovascular treatment aiding device 1 can have a constitution that does not require a sheath.

The material of the elastomer member 6 is not limited as long as the elastomer member 6 can have flexibility allowing changing of its outer diameter. The Shore hardness (Shore D) of the material according to ISO868:2003 is preferably 20 to 65 D. The material is preferably, but not limited to, a resin such as a polyurethane, silicone or polyamide elastomer.

Examples of the material constituting the filter 7 include polymers such as polyester, polyurethane, polyether urethane, polyamide, polyvinyl chloride, polycarbonate, polystyrene, polyethylene, polypropylene, polymethylpentene, polymethyl methacrylate, and polytetrafluoroethylene; and superelastic metals such as nickel alloys. The filter 7 is especially preferably constituted using polyester. In terms of the shape of the filter 7, the filter can be provided by preparing a polymer sheet, and forming a plurality of openings thereon. To increase the opening ratio of the filter to secure a sufficient blood passing rate, the filter 7 is more preferably prepared as a mesh using a polymer or a metal processed into a fiber. Examples of the polyester include polyethylene terephthalate (hereinafter referred to as "PET"), polytrimethylene terephthalate, polybutylene terephthalate, polyethylene naphthalate, and polybutylene naphthalate. Among these, PET is more preferred as the base material of the antithrombogenic material because of its versatility.

The pore size is not limited as long as capturing of thrombi or plaques is possible while the blood flow can be secured. When the filter 7 is formed as a sheet, the pore size is preferably 30 to 100 μm. When the filter 7 is formed as a mesh, each opening is preferably 30 to 100 μm on a side. Since the pore size is small, not only capturing of thrombi or plaques released from the vascular wall, but also formation of thrombi due to the filter 7, which is a foreign substance in the human body, may occur. Therefore, an antithrombogenic compound is preferably bound to the surface of the filter 7.

The material of the ring 8 is not limited as long as it is a flexible wire having elastic restoring force that allows free bending of the ring 8. The material is preferably a superelastic metal whose shape can be changed into various shapes, but can be restored to the original ring shape. The ring 8 can therefore be constituted of a shape-memory polymer. The ring 8 is more preferably constituted by a metal such as a nickel alloy.

The material of the supporting member 9 is not limited as long as the restoring force of the ring 8 is not inhibited, and the supporting member 9 is not broken by the bundling into the annular member 4. Examples of the material of the supporting member 9 include thin metal wires. The material of the supporting member 9 is more preferably a high-strength resin fiber such as an aramid fiber, polyarylate fiber, or polyester fiber.

In the filter section 3 of the example, the filter 7 and the supporting member 9 are fixed to each other through the ring 8. Alternatively, the supporting member 9 may be fixed directly, not through the ring 8, to the filter 7. In such a case, the supporting member 9 is preferably formed with a superelastic metal such as a nickel alloy.

The endovascular treatment aiding device is preferably one that suppresses thrombus formation caused thereby, and exerts high antithrombogenicity continuously for a long period. Antithrombogenicity means a property with which blood coagulation does not occur on the surface in contact with blood. For example, antithrombogenicity means a property that inhibits blood coagulation which proceeds due to platelet aggregation, activation of blood coagulation factors represented by thrombin, and/or the like.

The antithrombogenic compound means a compound having antithrombogenicity. In particular, an antithrombogenic compound needs to be bound to the surface of the filter 7, which has a large contacting area with blood and is prone to formation of thrombi.

Specific examples of the antithrombogenic compound include cationic polymers containing, as constituent monomers A, at least one compound selected from the group consisting of alkyleneimine, vinylamine, allylamine, lysine, protamine, and diallyldimethylam-monium chloride; and anionic sulfur compounds having anticoagulant activity.

The endovascular treatment aiding device is in a state where antithrombogenicity is given by covalent bonding of a cationic polymer to the surface of the filter 7, and binding of an anionic sulfur compound having anticoagulant activity to the filter 7 and/or the cationic polymer.

Since the constituent monomer A, which is a monomer constituting the cationic polymer, has a cationic nitrogen atom, the polymer is cationic. On the other hand, the compound having anticoagulant activity and containing a sulfur atom is anionic. Therefore, the polymer and the compound can be ionically bound to each other. Examples of the anionic sulfur compound having anticoagulant activity include heparin and heparin derivatives, dextran sulfate, polyvinyl sulfonate, and polystyrene sulfonate. Heparin and heparin derivatives are more preferred. The heparin and heparin derivatives may be either purified or unpurified, and are not limited as long as they can inhibit blood coagulation reaction. Examples of the heparin and heparin derivatives include heparins which are clinically generally and widely used, unfractionated heparins, and low-molecular-weight heparins, as well as heparins having high affinity to antithrombin III. Specific examples of the heparin include "heparin sodium" (manufactured by Organon API Inc.). Examples of the heparin derivatives include Fragmin, Crexane, Orgaran, and Arixtra.

Since cationic polymers have cationic properties, they may exhibit hemolytic toxicity and/or the like so that their elution into blood is not preferred. The cationic polymer is therefore preferably covalently bound to the surface of the filter 7. The covalent bonding of the cationic polymer to the surface of the filter 7 can be carried out by covalently binding a functional group of the cationic polymer to a functional group on the surface of the filter 7 by a well-known method. For example, the covalent bonding can be carried out by binding an amino group of the cationic polymer to a carboxyl group of a polyester constituting the filter 7, using a condensing agent such as 4-(4,6-dimethoxy-1,3,5-triazin-2-yl)-4-methylmorpholinium chloride n-hydrate ("DMT-MM"). As an alternative method, a method in which the cationic polymer is brought into contact with the filter 7 under heat to allow covalent bonding by amino lysis reaction may be used. Alternatively, radiation irradiation may be carried out to cause generation of radicals on the surface of the filter 7 and the cationic polymer, and covalent bonding between the surface of the filter 7 and the polymer may be achieved by recombination reaction of the radicals.

The covalent bond herein means a chemical bond formed by sharing of an electron(s) between atoms. The covalent bond is a covalent bond between atoms such as a carbon atom(s), nitrogen atom(s), oxygen atom(s), and/or sulfur atom(s) present in the cationic polymer and on the surface of the filter 7. The covalent bond may be either a single bond or a multiple bond. Examples of the type of the covalent bond include, but are not limited to, an amine bond, azide bond, amide bond, and imine bond. Among these, from the viewpoint of ease of formation of the covalent bond, stability after bonding, and the like, an amide bond is more preferred. As a result of intensive study, we discovered that, when amide bonds are formed between the cationic polymer and the surface of the filter 7, the configuration of the cationic polymer on the surface of the filter 7 optimizes the state of ionic bonding to the anionic sulfur compound having anticoagulant activity. Confirmation of the covalent bonds is possible by observation of the fact that elution does not occur by washing with a solvent that dissolves the polymer.

The cationic polymer may be either a homopolymer or a copolymer. When the cationic polymer is a copolymer, the copolymer may be any of a random copolymer, block copolymer, graft copolymer, and alternating copolymer. The cationic polymer is more preferably a block copolymer since, when the block copolymer has a block containing consecutive repeat units containing nitrogen atoms, the block portion interacts with the anionic sulfur compound having anticoagulant activity, to form strong ionic bonds.

The homopolymer herein means a macromolecular compound obtained by polymerization of a single kind of constituent monomers. The copolymer herein means a macromolecular compound obtained by copolymerization of two or more kinds of monomers. The block copolymer means a copolymer having a molecular structure in which at least two kinds of polymers having different repeat units are covalently bound to each other to form a longer chain. The block means each of the at least two kinds of polymers having different repeat units constituting the block copolymer.

The structure of the cationic polymer may be either linear or branched. The polymer is preferably branched since a branched polymer can form more stable ionic bonds at multiple positions with the anionic sulfur compound having anticoagulant activity.

The cationic polymer has at least one functional group selected from primary to tertiary amino groups and a quaternary ammonium group. In particular, the cationic polymer more preferably has a quaternary ammonium group rather than primary to tertiary amino groups since a quaternary ammonium group has stronger ionic interaction with the anionic sulfur compound having anticoagulant activity and, hence, allows easier control of the elution rate of the anionic sulfur compound having anticoagulant activity.

The carbon numbers of the three alkyl groups constituting the quaternary ammonium group are not limited. However, when the carbon numbers are too large, hydrophobicity is high, and steric hindrance is enhanced so that the anionic sulfur compound having anticoagulant activity cannot effectively bind to the quaternary ammonium group by ionic bonding. When the carbon number is too large, the polymer is more likely to show hemolytic toxicity so that the carbon number per alkyl group bound to the nitrogen atom constituting the quaternary ammonium group is preferably 1 to 12, more preferably 2 to 6. The carbon numbers of the three alkyl groups bound to the nitrogen atom constituting the quaternary ammonium group may be the same as or different from each other.

A polyalkyleneimine is preferably used as the cationic polymer since the amount of the anionic sulfur compound having anticoagulant activity adsorbed thereto by ionic interaction can be large. Examples of the polyalkyleneimine include polyethyleneimines (hereinafter referred to as "PEIs"), polypropyleneimines, and polybutyleneimines, as well as alkoxylated polyalkyleneimines. Among these, PEIs are more preferred.

Specific examples of the PEIs include "LUPASOL" (registered trademark) (manufactured by BASF) and "EPO-MIN" (registered trademark) (manufactured by Nippon Shokubai Co., Ltd.). The PEI may be a copolymer with other monomers, or may be a modified body, as long as the desired effect is not deteriorated. The modified body herein means a cationic polymer which has the same monomer repeat units constituting it, but has partially undergone, for example, radical decomposition or recombination due to radiation irradiation.

The cationic polymer may be composed only of at least one kind of constituent monomers selected from the group consisting of alkyleneimine, vinylamine, allylamine, lysine, protamine, and diallyldimethylammonium chloride. Alternatively, the cationic polymer may form a copolymer with one or more kinds of other monomers that do not adversely affect the antithrombogenicity. The other constituent monomers forming the copolymer are not limited, and examples of such monomers include constituent monomers B such as ethylene glycol, propylene glycol, vinylpyrrolidone, vinyl alcohol, vinylcaprolactam, vinyl acetate, styrene, methyl methacrylate, hydroxyethyl methacrylate, and siloxane. When the weight of the constituent monomers B is too high, the ionic bonding between the cationic polymer and the anionic sulfur compound having anticoagulant activity is weak. Therefore, the weight of the constituent monomers B with respect to the total weight of the cationic polymer is preferably not more than 10 wt %.

When the weight average molecular weight of the cationic polymer is too low, and lower than the molecular weight of the anionic sulfur compound having anticoagulant activity, stable ionic bonds cannot be formed so that the antithrombogenicity of interest is less likely to be obtained. On the other hand, when the weight average molecular weight of the cationic polymer is too high, the anionic sulfur compound having anticoagulant activity is included and embedded inside the cationic polymer. Thus, the weight average molecular weight of the cationic polymer is preferably 600 to 2,000,000, more preferably 1000 to 1,500,000, still more preferably 10,000 to 1,000,000. The weight average molecular weight of the cationic polymer can be measured by, for example, gel permeation chromatography or the light scattering method.

As a result of intensive study, we discovered that, from the viewpoint of suppressing thrombus formation caused by the endovascular treatment aiding device, and allowing exertion of high antithrombogenicity continuously for a long period, there is a preferred value of the abundance ratio of sulfur atoms to the abundance of total atoms on the surface of the filter 7 as measured by X-ray photoelectron spectroscopy (hereinafter referred to as "XPS"). The abundance ratio of atoms is expressed as "atomic percent." The atomic percent means the abundance ratio of a particular kind of atoms to the abundance of total atoms, which is taken as 100, in terms of the number of atoms.

That is, the abundance ratio of sulfur atoms to the abundance of total atoms on the surface of the filter 7 as measured by XPS is preferably 3.0 to 6.0 atomic percent, more preferably 3.2 to 5.5 atomic percent, still more preferably 3.5 to 5.0 atomic percent. When the abundance ratio of sulfur atoms to the abundance of total atoms is less than 3.0 atomic percent, the binding amount of the anionic sulfur compound having anticoagulant activity is small, and therefore the antithrombogenicity of interest required to suppress the thrombus formation due to the endovascular treatment aiding device is less likely to be obtained. On the other hand, when the abundance ratio of sulfur atoms to the abundance of total atoms is higher than 6.0 atomic percent, the binding amount of the anionic sulfur compound having anticoagulant activity is sufficient, and the antithrombogenicity of interest can therefore be obtained, but the amount of the cationic polymer covalently bound to the filter 7 for allowing the ionic bonding needs to be large. Moreover, as elution of the anionic sulfur compound having anticoagulant activity proceeds, the exposed cationic polymer may exhibit hemolytic toxicity and/or the like, which is not preferred.

More specifically, the abundance ratio of sulfur atoms to the abundance of total atoms on the surface of the filter 7 as measured by XPS can be determined by XPS.

Measurement Conditions
  Apparatus: ESCALAB 220iXL (manufactured by VG Scientific)
  Excitation X-ray: monochromatic AlK α1, 2 ray (1486.6 eV)
  X-ray diameter: 1 mm
  X-electron escape angle: 90° (the angle of the detector with respect to the surface of the filter 7)

The surface of the filter 7 as measured by XPS herein means the portion from the measurement surface to a depth of 10 nm as detected under the measurement conditions in XPS wherein the X-electron escape angle, that is, the angle of the detector with respect to the surface constituted by the antithrombogenic compound and the filter 7, is 90°. The filter 7 may or may not contain sulfur atoms.

By radiating X-ray to the surface of the filter 7, and measuring the energy of photoelectrons generated therefrom, the binding energy values of bound electrons in the substance can be obtained. From the binding energy values, information on the atoms on the surface of the filter 7 as measured by XPS can be obtained, and, from the energy shift of the peak at each binding energy value, information on the valence and the binding state can be obtained. In addition, by using the area ratio of each peak, quantification, that is, calculation of the abundance ratios of various atoms, valences, and binding states, is possible.

More specifically, the S2p peak, which indicates the presence of sulfur atoms, appears near a binding energy value of 161 eV to 170 eV. We discovered that the area ratio of the S2p peak in the whole peak area is preferably 3.0 to 6.0 atomic percent. In the calculation of the abundance ratio of sulfur atoms to the abundance of total atoms, the obtained value is rounded to one decimal place.

Similarly, we discovered that there is a preferred value of the abundance ratio of nitrogen atoms to the abundance of total atoms on the surface of the filter 7 as measured by XPS. That is, the abundance ratio of nitrogen atoms to the abundance of total atoms on the surface of the filter 7 as measured by XPS is preferably 7.0 to 12.0 atomic percent, more preferably 7.5 to 11.0 atomic percent, still more preferably 8.0 to 10.0 atomic percent. When the abundance ratio of sulfur atoms to the abundance of total atoms is less than 7.0 atomic percent, the amount of the cationic polymer bound to the filter 7 is small so that the antithrombogenicity of interest required to suppress thrombus formation due to the endovascular treatment aiding device is less likely to be obtained. On the other hand, when the abundance ratio of nitrogen atoms to the abundance of total atoms is higher than 12.0 atomic percent, the amount of the cationic polymer bound to the filter 7 is large so that the anionic sulfur compound having anticoagulant activity bound to the cationic polymer by ionic bonding is present in a sufficient amount. However, we found that, as elution of the anionic sulfur compound having anticoagulant activity proceeds, a large amount of the cationic polymer is exposed to show hemolytic toxicity. More specifically, the N1s peak, which indicates the presence of nitrogen atoms, appears near a binding energy value of 396 eV to 403 eV. We discovered that the area ratio of the N1s peak in the whole peak area is preferably 7.0 to 12.0 atomic percent. The N1s peak can be split mainly into the n1 component (near 399 eV), which is attributed to carbon-nitrogen (hereinafter referred to as "C—N") bonds; and the n2 component (near 401 to 402 eV), which is attributed to ammonium salt, C—N(structure different from n1), and/or nitrogen oxide (hereinafter referred to as "NO"). The abundance ratio of each split peak component can be calculated according to Equation (1). In this calculation, the abundance ratio of nitrogen atoms to the abundance of total atoms, and the abundance ratio of each split peak component, are rounded to one decimal place.

$$\text{Split}_{ratio} = \text{N1s}_{ratio} \times (\text{Split}_{percent}/100) \quad (1)$$

$\text{Split}_{ratio}$: abundance ratio of each split peak component (%)
  $\text{N1s}_{ratio}$: abundance ratio of nitrogen atoms to the abundance of total atoms (%)
  $\text{Split}_{percent}$: abundance ratio of each split peak component in the N1s peak (%)

The n2 component, which is attributed to NO, obtained by splitting the N1s peak indicates the presence of quaternary ammonium groups. We discovered that the abundance ratio of the n2 component in the total component of the N1s peak, that is, $\text{Split}_{percent}$ (n2), is preferably 20 to 70 atomic percent, more preferably 25 to 65 atomic percent, still more preferably 30 to 60 atomic percent. When $\text{Split}_{percent}$ (n2) is less than 20 atomic percent, the abundance of quaternary ammonium groups is low. Therefore, the ionic interaction with the anionic sulfur compound having anticoagulant activity is weak, and the elution rate is therefore high so that the antithrombogenicity of interest required for suppressing the thrombus formation due to the endovascular treatment aiding device is less likely to be obtained. On the other hand, when $\text{Split}_{percent}$ (n2) is higher than 70 atomic percent, the ionic interaction with the anionic sulfur compound having anticoagulant activity is too strong. In such cases, because of a decrease in the degree of freedom due to formation of ionic complexes, it is impossible to maintain a high anticoagulant activity for a long period, and the elution rate tends be low.

Because of the above reasons, the abundance ratio of the n2 component, that is, $\text{Split}_{ratio}$ (n2), which is calculated according to Equation (1), is preferably 1.4 to 8.4 atomic percent, more preferably 1.8 to 7.2 atomic percent, still more preferably 2.4 to 6.0 atomic percent.

The C1s peak, which indicates the presence of carbon atoms, appears near a binding energy value of 282 to 292 eV. The C1s peak can be split mainly into the c1 component (near 285 eV), which is attributed to carbon-hydrogen (hereinafter referred to as "CHx") bonds suggesting the presence of a saturated hydrocarbon(s) and/or the like, to carbon-carbon (hereinafter referred to as "C—C") bonds, and/or to carbon=carbon (hereinafter referred to as "C=C") bonds; the c2 component (near 286 eV), which is attributed to carbon-oxygen (hereinafter referred to as "C—O") bonds suggesting the presence of an ether(s) and/or hydroxyl groups, and/or to carbon-nitrogen (hereinafter referred to as "C—N") bonds; the c3 component (near 287 to 288 eV), which is attributed to carbon=oxygen (hereinafter referred to as "C=O") bonds suggesting the presence of carbonyl groups; the c4 component (near 288 to 289 eV), which is attributed to oxygen=carbon-oxygen (hereinafter referred to as "O=C—O") bonds suggesting the presence of ester groups and/or carboxyl groups; and the c5 component (near 290 to 292 eV), which is attributed to π-π* satellite peak (hereinafter referred to as "η-η") bonds suggesting the presence of a conjugated system(s) such as benzene rings. The abundance ratio of each split peak component can be calculated according to Equation (2). In this calculation, the abundance ratio of carbon atoms to the abundance of total atoms, and the abundance ratio of each split peak component, are rounded to one decimal place.

$$\text{Split}_{ratio} = C1s_{ratio} \times (\text{Split}_{percent}/100) \quad (2)$$

$\text{Split}_{ratio}$: abundance ratio of each split peak component (%)

$C1s_{ratio}$: abundance ratio of carbon atoms to the abundance of total atoms (%)

$\text{Split}_{percent}$: abundance ratio of each split peak component in the C1s peak (%)

The c3 component, which is attributed to C=O bonds, obtained by splitting the C1s peak indicates the presence of amide groups. We discovered that the abundance ratio of the c3 component in the total component of the C1s peak, that is, the abundance ratio of amide groups, is preferably not less than 2.0 atomic percent, more preferably not less than 3.0 atomic percent. When the abundance ratio of the amide groups is less than 2.0 atomic percent, the number of covalent bonds due to amide bonds between the cationic polymer and the filter 7 is small, and therefore the binding amount of the cationic polymer is small. Moreover, since the state of ionic bonding between the cationic polymer and the anionic sulfur compound having anticoagulant activity is poor, the antithrombogenicity of interest is less likely to be obtained.

In addition, as another/other antithrombogenic material(s),
    an anionic polymer(s) containing, as constituent monomers, at least one compound selected from the group consisting of acrylic acid, methacrylic acid, α-glutamic acid, γ-glutamic acid, and aspartic acid; and/or
    at least one anionic compound selected from the group consisting of dicarboxylic acids such as oxalic acid, malonic acid, succinic acid, fumaric acid, glutaric acid, adipic acid, pimelic acid, suberic acid, azelaic acid, sebacic acid, malic acid, tartaric acid, and dodecanedioic acid, and citric acid;

is/are preferably bound to the filter 7 and/or the cationic polymer. The anionic polymer(s) and/or anionic compound(s) can be bound to the cationic polymer by ionic bonding.

The anionic polymer is preferably, but does not necessarily need to be, a polyacrylic acid (hereinafter referred to as "PAA"), polymethacrylic acid, poly(α-glutamic acid), poly (γ-glutamic acid), or polyaspartic acid since, in cases where the weight ratio of anionic functional groups is high, the amount of the anionic polymer bound to the filter 7 can be large. The anionic polymer is more preferably a PAA.

Specific examples of the PAA include "polyacrylic acid" (manufactured by Wako Pure Chemical Industries, Ltd.). The PAA may be a copolymer with other monomers, or may be a modified body as long as the desired effect is not deteriorated.

From the viewpoint of safety and the like, elution of the anionic polymer into blood is not preferred. Thus, the anionic polymer is preferably bound, more preferably covalently bound, to the surface of the filter 7.

The anionic polymer may be either a homopolymer or a copolymer. When the anionic polymer is a copolymer, the copolymer may be any of a random copolymer, block copolymer, graft copolymer, and alternating copolymer.

The anionic polymer may be constituted only by the constituent monomers described above, or may form a copolymer with constituting monomers other than those described above as long as the antithrombogenicity is not adversely affected. The constituent monomers other than acrylic acid, methacrylic acid, α-glutamic acid, γ-glutamic acid, and aspartic acid to be used to form the copolymer are not limited, and examples of such monomers include constituent monomers B such as ethylene glycol, propylene glycol, vinylpyrrolidone, vinyl alcohol, vinylcaprolactam, vinyl acetate, styrene, methyl methacrylate, hydroxyethyl methacrylate, and siloxane. When the weight of the constituent monomers B is too high, the number of reaction sites for binding to the filter 7 or to the other antithrombogenic compound(s) is small. Accordingly, the weight of the constituent monomers B with respect to the total weight of the anionic polymer is preferably not more than 10 wt %.

The anionic compound is preferably, but does not necessarily need to be, at least one selected from the group consisting of oxalic acid, malonic acid, succinic acid, fumaric acid, glutaric acid, adipic acid, pimelic acid, suberic acid, azelaic acid, sebacic acid, malic acid, tartaric acid, and citric acid since, in cases where the weight ratio of anionic functional groups is high, a larger amount of the anionic compound can be bound to the filter 7 or the other antithrombogenic compound(s). The anionic compound is more preferably succinic acid.

When the weight average molecular weight of the anionic polymer is too small, the amount of the polymer bound to the filter 7 or to the other antithrombogenic compound(s) is small. It is therefore difficult to obtain a high and long-lasting antithrombogenicity. On the other hand, when the weight average molecular weight of the anionic polymer is too high, the antithrombogenic compound is included in the inside. Therefore, the weight average molecular weight of the anionic polymer is preferably 600 to 2,000,000, more preferably 10,000 to 1,000,000.

The surface amount of the anionic sulfur compound having anticoagulant activity on the filter 7 after soaking in physiological saline at 37° C. for 30 minutes was measured based on the anti-factor Xa activity. The anti-factor Xa activity is an index indicating the degree of inhibition of the activity of factor Xa, which promotes conversion of prothrombin to thrombin. By this, the surface amount of the compound can be known in terms of the unit of activity. For the measurement, "Test Team (registered trademark) Heparin S" (manufactured by Sekisui Medical Co., Ltd.) (hereinafter referred to as Test Team Heparin) was used. When the anti-factor Xa activity is too low, the surface amount of the anionic sulfur compound having anticoagulant activity on the filter 7 is small so that the antithrombogenicity of interest is less likely to be obtained. That is, the anti-factor Xa activity is preferably 30 mIU/cm$^2$, more preferably 50 mIU/cm$^2$. More specifically, the surface amount was measured as follows. The filter 7 to which the anionic sulfur compound having anticoagulant activity is bound was cut into a test piece having an effective surface area of about 0.26 cm$^2$, and the test piece was then soaked in 0.5 mL of physiological saline at 37° C. for 30 minutes. To the filter 7 after the soaking, 0.02 mL of human blood plasma, 0.02 mL of the antithrombin III liquid in Test Team Heparin, and 0.16 mL of a buffer were added to provide a sample, and the sample was then allowed to react according to the operation procedure for Test Team Heparin (end-point method). The absorbance at 405 nm was measured using a microplate reader (MTP-300, manufactured by Corona Electric Co., Ltd.). Using a calibration curve separately prepared using Heparin Sodium Injection (manufactured by Ajinomoto Pharmaceuticals Co., Ltd.), the surface amount was calculated. The heating time of the sample in the end-point method was 6 minutes.

The endovascular treatment aiding device is characterized in that, irrespective of the fact that the total binding amount of the anionic sulfur compound having anticoagulant activity on the filter 7 as measured based on the anti-factor Xa activity is small, the surface amount after soaking in physiological saline at 37° C. for 30 minutes is large. The total binding amount herein is the sum of the amount of the anionic sulfur compound having anticoagulant activity eluted in human blood plasma (product number, 12271210; manufactured by COSMO BIO Co., Ltd.) after 24 hours of soaking in the human blood plasma at 37° C., as calculated based on the anti-factor Xa activity, and the surface amount of the anionic sulfur compound having anticoagulant activity on the filter 7 after the 24 hours of soaking, as calculated based on the anti-factor Xa activity. More specifically, the amount of the anionic sulfur compound having anticoagulant activity eluted as calculated based on the anti-factor Xa activity was evaluated as follows. The filter 7 to which the anionic sulfur compound having anticoagulant activity is bound was cut into a test piece having an effective surface area of about 4.24 cm$^2$, and the test piece was then soaked in 1.5 mL of human blood plasma at 37° C. for 24 hours. To 0.04 mL of the resulting human blood plasma, 0.04 mL of the antithrombin III liquid in Test Team Heparin and 0.32 mL of a buffer were added to provide a sample, and the sample was then allowed to react according to the operation procedure for Test Team Heparin (end-point method). The absorbance at 405 nm was measured using a microplate reader. Using a calibration curve separately prepared using Heparin Sodium Injection, the amount of the anionic sulfur compound having anticoagulant activity eluted was calculated. The heating time of the sample in the end-point method was 5 minutes. The surface amount of the anionic sulfur compound having anticoagulant activity on the filter 7 after the 24 hours of soaking, as calculated based on the anti-factor Xa activity, was determined in the same manner as the surface amount of the anionic sulfur compound having anticoagulant activity on the filter 7 after soaking in physiological saline at 37° C. for 30 minutes as calculated based on the anti-factor Xa activity, except that the filter 7 after the 24 hours of soaking was used.

When the total binding amount is too large, the microstructure on the surface of the filter 7 is destroyed, while when the total binding amount is too small, the antithrombogenicity of interest is less likely to be obtained. That is, preferably, the total binding amount of the anionic sulfur compound having anticoagulant activity on the filter 7 as measured based on the anti-factor Xa activity is not more than 10,000 mIU/cm$^2$, and the surface amount of the anionic sulfur compound having anticoagulant activity on the filter 7 after soaking in physiological saline at 37° C. for 30 minutes as calculated based on the anti-factor Xa activity is not less than 30 mIU/cm$^2$. More preferably, the total binding amount is not more than 5000 mIU/cm$^2$, and the surface amount is not less than 50 mIU/cm$^2$.

The endovascular treatment aiding device is characterized in the elution behavior of the anionic sulfur compound having anticoagulant activity on the filter 7. That is, elution of the anionic sulfur compound having anticoagulant activity hardly occurs when the filter 7 is soaked in physiological saline at 37° C., while the elution rapidly occurs when the filter 7 is soaked in human blood plasma (product number, 12271210; manufactured by COSMO BIO Co., Ltd.) at 37° C. More specifically, during 1 hour of soaking in human blood plasma at 37° C., elution of not less than 50%, more preferably not less than 70%, still more preferably not less than 80%, of the total binding amount occurs. Similarly, during 15 minutes of soaking, elution of not less than 50%, more preferably not less than 70%, still more preferably not less than 80%, of the total binding amount occurs.

In terms of the range of the thickness of the antithrombogenic compound layer, when the layer is too thick, the microstructure on the surface of the filter 7 is destroyed and, moreover, thrombus formation may occur due to the change in the pore size and the change in the outer diameter of the opening-section side in the state where the filter section 3 is closed. That is, the thickness is preferably 1 to 600 nm.

The thickness of the antithrombogenic compound layer herein can be determined by, for example, combination of a scanning transmission electron microscope (hereinafter referred to as "STEM"), XPS and/or the like. More specifically, when observation of the atomic distribution in the vertical direction from the interface of the filter 7 toward the inside is carried out, the thickness of the antithrombogenic compound layer means the distance from the start point to the end point of the range in which atoms derived from the antithrombogenic material layer are found. The thickness is measured as the mean of thickness values observed at at least three points.

The interface of the filter 7 as measured by STEM herein means the boundary between the acrylic resin or the like used to embed the filter 7 in the sample preparation before the measurement by STEM, and the surface of the layer composed of the filter 7 and the antithrombogenic compound.

More specifically, STEM has detectors such as an energy dispersive X-ray spectrometer (hereinafter referred to as "EDX") and an electron energy-loss spectrometer (hereinafter referred to as "EELS"). Measurement conditions for the STEM are as follows.

Measurement Conditions
    Apparatus: field emission transmission electron microscope JEM-2100F (manufactured by JEOL Ltd.)
    EELS detector: GIF Tridiem (manufactured by GATAN, Inc.)
    EDX detector: JED-2300T (manufactured by JEOL Ltd.)
    Image acquisition: Digital Micrograph (manufactured by GATAN, Inc.)
    Sample preparation: ultrathin sectioning (suspension using a copper microgrid; use of an
    acrylic resin as an embedding resin)
    Acceleration voltage: 200 kV
    Beam diameter: 0.7-nm diameter
    Energy resolution: about 1.0 eV FWHM The presence of each kind of atoms is judged based on whether a peak intensity derived from the atoms can be found in a spectrum obtained by STEM measurement after subtraction of the background.

EXAMPLES

Examples of the endovascular treatment aiding device 1 are concretely described below with reference to figures. Our tools are described below in detail by way of Examples and Comparative Examples. However, this disclosure is not limited thereto.

Example 1

An endovascular treatment aiding device 1 according to FIG. 1 was prepared. More specifically, the filter 7 was constituted by a mesh using monofilament polyester (PET) fibers having a fiber diameter of 28 µm such that the pore size was 100 µm on a side. This mesh was prepared such that the length in the longitudinal direction was about 8 mm, and the circular diameter of the opening section of the filter section 3 was 4 mm.

The ring 8 was prepared using a NiTi alloy wire having a wire diameter of 42 µm by triple winding such that the inner diameter was 4 mm. The inner-diameter portion of the ring 8 was fixed to the outer diameter of the opening section of the filter 7.

For the supporting member 9, aramid fibers having a fiber diameter of about 60 µm were used. The filter section 3 was prepared by binding each fiber to both the ring 8 and the filter 7 such that the fibers were fixed in the positional relationship shown in FIG. 2, wherein the circumference of the ring 8 was equally divided into four segments.

For the shaft 2, a stainless-steel wire having an outer diameter of 0.2 mm and a length in the longitudinal direction of 1800 mm was used. A taper shape was given to the wire such that the outer diameter of the portion from the distal end a position about 20 mm distant therefrom in the longitudinal direction was 0.06 mm to 0.15 mm; the outer diameter of the shaft 2 in the next portion having a length of about 30 mm was 0.15 mm; and the outer diameter in the further next portion having a length of 20 mm was 0.15 mm to 0.2 mm, to prepare the shaft 2.

The shaft 2 was arranged such that it coaxially passed through the closed-end section and the opening section of the filter section 3 and the polyimide tube bundling the supporting member, and such that the entire supporting member 9 had a uniform length, that is, such that the shaft 2 was positioned on the central axis of the ring 8. On the portion of the shaft 2 having an outer diameter of 0.15 mm, the supporting member 9 was fixed to the shaft 2 using a polyimide tube having an inner diameter of 0.25 mm, an outer diameter of 0.29 mm, and a length of 1.5 mm, with an adhesive.

The annular member 4 was prepared by molding using a polypropylene such that it had a total length was 2.5 mm and an inner diameter of 0.4 mm; the outer diameter of the portion other than the thick section 4a was 0.5 mm; the thick section 4a was arranged in the area from the position 0.7 mm distant from the proximal side of the annular member 4, along a width of 0.2 mm from the distal side; and the outer diameter of the thick section 4a was 0.75 mm. The annular member 4 was arranged on the shaft 2 as shown in FIG. 1 such that the thick section 4a was positioned closer to the proximal side of the annular member 4.

The outer tube 5 was prepared such that it had a three-layer structure composed of a polytetrafluoroethylene inner layer, a braided layer of stainless-steel flat rectangular wires as an intermediate layer, and a polyimide outer layer, and had an inner diameter of 0.23 mm, an outer diameter of 0.36 mm, and a length of 1500 mm. To the distal end of the outer tube 5, a polyimide tube having an inner diameter of 0.4 mm, an outer diameter of 0.52 mm, and a length of 0.5 mm was fixed using an adhesive such that the end portions of the outer tube 5 and the polyimide tube joined together.

The elastomer member 6 was prepared using a polyamide elastomer having a Shore hardness of about 55 D such that it had an inner diameter of 0.55 mm, an outer diameter of 0.7 mm, and a total length of 1.5 mm. To the polyimide tube adhered to the distal end of the outer tube 5, a portion with a length of 0.5 mm in the elastomer member 6 was adhered using an adhesive such that the remaining portion of the elastomer member 6 with a length of 1 mm protruded from the outer tube 5.

The member composed of the combination of the outer tube 5 and the elastomer member 6 was arranged on the shaft 2 such that the elastomer member 6 was positioned in the distal side in the longitudinal direction, to prepare the endovascular treatment aiding device 1. The outer diameter, in the direction vertical to the longitudinal direction, of the opening section of the filter section 3 in the state where the filter section 3 of the endovascular treatment aiding device 1 was closed was about 0.8 mm, and the outer diameter, in the direction vertical to the longitudinal direction, of the end face of the elastomer member 6 in the state where the elastomer member 6 covered the thick section 4a of the annular member 4 was about 1 mm.

Comparative Example 1

Figure 4:
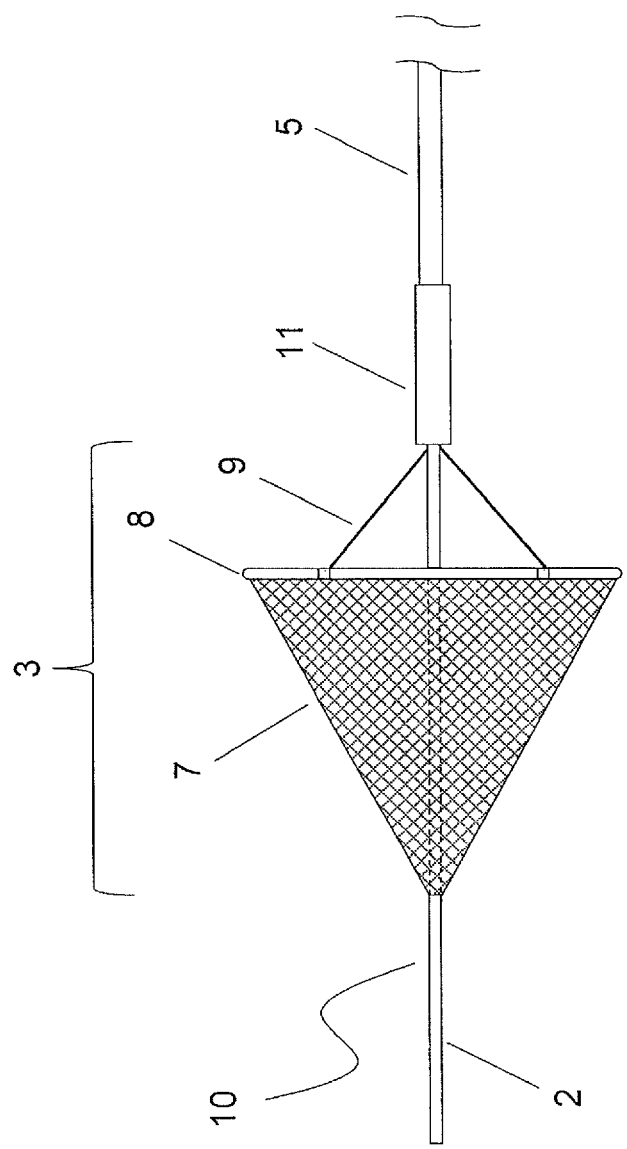
FIG. 4 is a schematic view showing a side view, in the longitudinal direction, of the endovascular treatment aiding device according to Comparative Example 1.

As Comparative Example 1, an endovascular treatment aiding device 10 having no thick section 4a in the annular member was prepared as shown in FIG. 4. More specifically, the same endovascular treatment aiding device as in the Example was prepared except that an annular member 11 using a polyimide tube having an inner diameter of 0.4 mm, an outer diameter of 0.52 mm, and a length of 3.5 mm was used instead of the annular member 4, and that the elastomer member was not used. Preparation of the endovascular treatment aiding device 10 was carried out in exactly the same manner as in the Example except that the annular member 11 was adhered to the outer tube 5 such that a 3-mm portion protruded therefrom, and that the resultant was arranged on the shaft 2 such that the side with the annular member 11 was positioned in the distal side. In the endovascular treatment aiding device 10 of Comparative Example 1, the outer diameter, in the direction vertical to the longitudinal direction, of the opening section of the filter section 3 in the state where the filter section 3 was closed was about 0.8 mm, similarly to the Example.

Comparative Example 2

Filtrap (registered trademark) FTS-35-18S, which is a thrombus capturing catheter manufactured by NIPRO, in which a plurality of supporting members are spirally intersecting each other on a shaft; the supporting members are bundled at their tips and their proximal ends; the intermediate portion of the supporting members has an expanded spindle shape; and the end-portion side corresponding to the half of the spindle shape in the distal end portion is covered with a filter fixed thereto, to constitute a parachute-like filter section; was provided as Comparative Example 2. Comparative Example 2 was an endovascular treatment aiding device having a maximum filter expansion diameter of 3.5 mm, a shaft length of 1800 mm, and a shaft diameter of 0.36 mm, which is retrieved using a retrieval sheath. The outer diameter of the portion in the retrieval sheath where the filter section is to be contained was 1.1 mm, and the outer diameter of the opening section of the filter section in the closed state was slightly larger than 1.1 mm.

Comparative Experiments on Catching of Endovascular Treatment Aiding Device During Retrieval To carry out comparative experiments, a guiding catheter for 6 Fr was inserted from Femoral approach (whose description is available in the product) using a PCI TRAINER for BEGINNERS (commercially available from Medialpha), which is a two-dimensional blood vessel model, and the distal end of the guiding catheter was placed at the inlet of the portion corresponding to the coronary artery in the two-dimensional blood vessel. In the middle of the coronary artery model, a stent was placed, and the endovascular treatment aiding device of Example or Comparative Example 1 or 2 was allowed to pass through the inside of the guiding catheter and the stent, to place the filter section in the distal side relative to the stent.

In this state, comparative experiments were carried out in 10 replicates for each experiment to investigate whether or not the endovascular treatment aiding devices of Example and Comparative Examples 1 and 2 are caught in the stent or the guiding catheter during retrieval of the devices.

As a result, in Example, catching in the stent or the guiding catheter did not occur at all in the 10 replicates of the experiment. On the other hand, in Comparative Example 1, catching in the stent occurred once in the 10 replicates of the experiment, and catching in the distal end of the guiding catheter occurred three times in the 10 replicates of the experiment. In Comparative Example 2, the retrieval sheath could not pass through the vascular bifurcation before the coronary artery model in which the stent is placed, in all of the 10 replicates of the experiment. Thus, the retrieval sheath could not reach the filter section.

Example 2

Endovascular treatment aiding devices 1 according to FIG. 1 were prepared. More specifically, a mesh was prepared with monofilament polyester (PET) fibers having a fiber diameter of 28 μm such that the pore size was 100 μm on a side.

Subsequently, the mesh was soaked in an aqueous solution of 5.0 wt % potassium permanganate (manufactured by Wako Pure Chemical Industries, Ltd.) and 0.6 mol/L sulfuric acid (manufactured by Wako Pure Chemical Industries, Ltd.), and the reaction was allowed to proceed at 60° C. for 3 hours, thereby hydrolyzing and oxidizing the mesh (step of hydrolysis and oxidation). The aqueous solution after the reaction was removed, and the mesh was washed with hydrochloric acid (manufactured by Wako Pure Chemical Industries, Ltd.) and distilled water.

Subsequently, the mesh was soaked in an aqueous solution of 0.5 wt % 4-(4,6-dimethoxy-1,3,5-triazin-2-yl)-4-methylmorpholinium chloride n-hydrate (hereinafter referred to as "DMT-MM") (condensing agent) (manufactured by Wako Pure Chemical Industries, Ltd.) and 5.0 wt % PEI (LUPASOL (registered trade mark) P, manufactured by BASF), followed by allowing the reaction to proceed at 30° C. for 2 hours, thereby covalently binding PEI to the mesh by condensation reaction (first coating step). The aqueous solution after the reaction was removed, and the mesh was washed with distilled water.

The mesh was further soaked in 1 wt % aqueous methanol solution of ethyl bromide (manufactured by Wako Pure Chemical Industries, Ltd.) or pentyl bromide (manufactured by Wako Pure Chemical Industries, Ltd.), and the reaction was allowed to proceed at 35° C. for 1 hour, and then at 50° C. for 4 hours, thereby allowing modification of PEI covalently bound to the surface of the mesh with quaternary ammonium (quaternary ammonium modification step). The aqueous solution after the reaction was removed, and the mesh was washed with methanol and distilled water.

Finally, the mesh was soaked in an aqueous solution (pH=4) of 0.75 wt % heparin sodium (manufactured by Organon API Inc.) and 0.1 mol/L sodium chloride, and the reaction was allowed to proceed at 70° C. for 6 hours, thereby allowing ionic bonding with PEI (second coating step). The aqueous solution after the reaction was removed, and the mesh was washed with distilled water.

A mesh treated with PEI (average molecular weight, about 600; manufactured by Wako Pure Chemical Industries, Ltd.) and ethyl bromide was provided as Mesh A; a mesh treated with PEI (LUPASOL (registered trade mark) P, manufactured by BASF), but not subjected to the quaternary ammonium modification step was provided as Mesh B; a mesh treated with PEI (LUPASOL (registered trade mark) P, manufactured by BASF) and ethyl bromide was provided as Mesh C; and a mesh treated with PEI (LUPASOL (registered trade mark) P, manufactured by BASF) and pentyl bromide was provided as Mesh D.

Using Meshes A to D, filters 7 having a length in the longitudinal direction of about 8 mm and a circular diameter of the opening-section side of 4 mm were prepared to provide Sample A, Sample B, Sample C, and Sample D, respectively. In Example 1, Samples A to D were used as filters 7.

The ring 8 was prepared using a nickel-titanium alloy wire having a wire diameter of 42 μm by triple winding such that the inner diameter was 4 mm. The inner-diameter portion of the ring 8 was fixed to the outer diameter of the opening section of the filter 7 using polyurethane.

For the supporting member 9, four polyacrylate fibers having a fiber diameter of about 60 μm were used. The filter section 3 was prepared by binding each fiber to both the ring 8 and the filter 7 such that the fibers were fixed in the positional relationship shown in FIG. 2, wherein the circumference of the ring 8 was equally divided into four segments.

For the shaft 2, a stainless-steel wire having an outer diameter of 0.2 mm and a length in the longitudinal direction of 1800 mm was used. A taper shape was given to the portion from the distal end to a position about 20 mm distant therefrom in the longitudinal direction; the outer diameter of the next portion in the shaft 2 having a length of about 30 mm was adjusted to 0.15 mm; and a taper shape was given to the further next portion having a length of 20 mm.

The shaft 2 was arranged such that it penetrated the closed-end section and the opening section of the filter section 3 and the polyimide tube bundling the supporting member 9, and such that the entire supporting member 9 had a uniform length, that is, such that the shaft 2 was positioned on the central axis of the ring 8. On the portion of the shaft 2 having an outer diameter of 0.15 mm, the supporting member 9 was fixed to the shaft 2 using a polyimide tube having an inner diameter of 0.25 mm, an outer diameter of 0.29 mm, and a length of 1.5 mm, using an adhesive.

The annular member 4 was prepared by molding using a polypropylene such that it had a total length of 2.5 mm and an inner diameter of 0.4 mm; the outer diameter of the portion other than the thick section 4a was 0.5 mm; the thick section 4a was arranged in the area from the position 0.7 mm distant from the proximal side in the longitudinal direction of the annular member 4, along a width of 0.2 mm from the distal side in the longitudinal direction; and the outer diameter of the thick section 4a was 0.75 mm. The annular member 4 was arranged on the shaft 2 as shown in FIG. 1 such that the thick section 4a was positioned closer to the proximal side of the annular member 4.

The outer tube 5 was prepared such that it had a three-layer structure composed of a polytetrafluoroethylene inner layer, a braided layer of stainless-steel flat rectangular wires as an intermediate layer, and a polyimide outer layer, and had an inner diameter of 0.23 mm, an outer diameter of 0.36 mm, and a length of 1500 mm. To the distal end of the outer tube 5, a polyimide tube having an inner diameter of 0.4 mm, an outer diameter of 0.52 mm, and a length of 0.5 mm was fixed using an adhesive such that the end portions of the outer tube 5 and the polyimide tube joined together.

The elastomer member 6 was prepared using a polyamide elastomer having a Shore hardness of about 55 D such that it had an inner diameter of 0.55 mm, an outer diameter of 0.7 mm, and a total length of 1.5 mm. To the polyimide tube adhered to the distal end of the outer tube 5, a portion with a length of 0.5 mm in the elastomer member 6 was adhered using an adhesive such that the remaining portion of the elastomer member 6 with a length of 1 mm protruded from the outer tube 5.

The member composed of the combination of the outer tube 5 and the elastomer member 6 was arranged on the shaft 2 such that the elastomer member 6 was positioned in the distal side in the longitudinal direction, to prepare the endovascular treatment aiding device 1. The outer diameter, in the direction vertical to the longitudinal direction, of the opening section of the filter section 3 in the state where the filter section 3 of the endovascular treatment aiding device 1 was closed was about 0.8 mm, and the outer diameter, in the direction vertical to the longitudinal direction, of the end face in the distal side in the longitudinal direction of the elastomer member 6 in the state where the elastomer member 6 covered the thick section 4a of the annular member 4 was about 1 mm.

For the endovascular treatment aiding device 1 using Sample A as the filter 7, a comparative experiment on catching of the endovascular treatment aiding device during its retrieval was carried out. The results are shown in Table 1. As shown in Table 1, catching in the stent or the guiding catheter did not occur at all in 10 replicates of the experiment.

Samples A to D used for endovascular treatment aiding devices 1 were subjected to evaluation by the human whole blood test. The results are shown in Table 2. As shown in Table 2, no thrombus adhesion (−) was found for Sample A, and no thrombus adhesion (−−) was found for Samples B to D, in the evaluation by the human whole blood test.
Example 3

The first coating step was carried out by the same operation as in Mesh B in Example 2, and the mesh was then soaked in a solution of 0.5 wt % DMT-MM and 40 wt % succinic anhydride (manufactured by Wako Pure Chemical Industries, Ltd.) in dimethylacetamide, followed by allowing the reaction to proceed at 50° C. for 17 hours (first additional step). The solution after the reaction was removed, and the mesh was washed with methanol and distilled water.

The mesh was further immersed in an aqueous solution of 0.5 wt % DMT-MM and 5.0 wt % PEI, and the reaction was allowed to proceed at 30° C. for 2 hours (second additional step). The aqueous solution after the reaction was removed, and the mesh was washed with distilled water. The quaternary ammonium modification step using ethyl bromide was carried out by the same operation as in Mesh C in Example 2, and the second coating step was then carried out. The same reagents as in Example 2 were used except for the antithrombogenic compound.

A filter 7 prepared with a mesh subjected to the second additional step using PEI (LUPASOL (registered trade mark) P, manufactured by BASF) was provided as Sample E, and a filter 7 prepared with a mesh subjected to the second additional step using PEI (LUPASOL (registered trade mark) SK, manufactured by BASF) was provided as Sample F.

Samples E and F used for endovascular treatment aiding devices 1 were subjected to evaluation by the human whole blood test. The results are shown in Table 2. As shown in Table 2, no thrombus adhesion (−−) was found in the evaluation by the human whole blood test.
Example 4

The first coating step was carried out by the same operation as in the case of Mesh B in Example 2, and the mesh was then soaked in an aqueous solution of 0.5 wt % DMT-MM and 0.5 wt % PAA (manufactured by Wako Pure Chemical Industries, Ltd.), followed by allowing the reaction to proceed at 30° C. for 2 hours (first additional step). The aqueous solution after the reaction was removed, and the mesh was washed with an aqueous sodium carbonate solution and distilled water.

The mesh was further soaked in an aqueous solution of 0.5 wt % DMT-MM and 5.0 wt % PEI, and the reaction was allowed to proceed at 30° C. for 2 hours (second additional step). The aqueous solution after the reaction was removed, and the mesh was washed with distilled water. The quaternary ammonium modification step using ethyl bromide was carried out by the same operation as in Mesh C in Example 2, and the second coating step was then carried out. The same reagents as in Example 2 were used except for the antithrombogenic compound.

A filter 7 prepared with a mesh subjected to the second additional step using PEI (average molecular weight, about 600; manufactured by Wako Pure Chemical Industries, Ltd.) was provided as Sample G; a filter 7 prepared with a mesh subjected to the second additional step using PEI (LUPASOL (registered trade mark) P, manufactured by BASF) was provided as Sample H; and a filter 7 prepared with a mesh subjected to the second additional step using poly(allylamine hydrochloride) (hereinafter referred to as "PAH") (weight average molecular weight, 900,000; manufactured by Sigma-Aldrich) was provided as Sample I.

Samples G to I used for endovascular treatment aiding devices 1 were subjected to evaluation by the human whole blood test. The results are shown in Table 2. As shown in Table 2, no thrombus adhesion (−−) was found in the evaluation by the human whole blood test.
Example 5

The first coating step was carried out by the same operation as in Example 2 except that PAH (weight average molecular weight, 900,000; manufactured by Sigma-Aldrich) or poly-L-lysine hydrobromide (hereinafter referred to as PLys) (average molecular weight, 30,000 to 70,000; manufactured by Sigma-Aldrich) was used instead of PEI. The quaternary ammonium modification step using ethyl bromide was carried out by the same operation as in Mesh C in Example 2 using ethyl bromide, and the second coating step was then carried out. The same reagents as in Example 2 were used except for the antithrombogenic compound.

A filter 7 prepared with a mesh subjected to the first coating step using PAH instead of PEI was provided as Sample J, and a filter 7 prepared with a mesh subjected to the first coating step using PLys instead of PEI was provided as Sample K. The same reagents as in Example 2 were used except for the antithrombogenic compound.

Samples J and K used for endovascular treatment aiding devices 1 were subjected to evaluation by the human whole blood test. The results are shown in Table 2. As shown in Table 2, no thrombus adhesion (−) was found in the evaluation by the human whole blood test.

Example 6

A filter 7 prepared with a mesh subjected to the second coating step by the same operation as in Mesh C in Example 2 except that dextran sulfate sodium (Wako Pure Chemical Industries, Ltd.) was used instead of heparin sodium (manufactured by Organon API Inc.) was provided as Sample L. The same reagents as in Example 2 were used except for the antithrombogenic compound.

Sample L used for an endovascular treatment aiding device 1 was subjected to evaluation by the human whole blood test. The results are shown in Table 2. As shown in Table 2, no thrombus adhesion (−) was found in the evaluation by the human whole blood test.

Example 7

A mesh was soaked in an aqueous solution of 5% PEI, and irradiated with 5 kGy of γ-ray using a type JS-8500 Cobalt 60 γ-ray irradiator (manufactured by Nordion International Inc.) to allow covalent bonding (first coating step). The aqueous solution after the reaction was removed, and the mesh was washed with Triton-X100 (manufactured by Sigma-Aldrich), physiological saline, and distilled water. The quaternary ammonium modification step using ethyl bromide was carried out by the same operation as in Mesh C in Example 2, and the second coating step was then carried out. The same reagents as in Example 2 were used except for the antithrombogenic compound.

A filter 7 prepared with a mesh treated with PEI (average molecular weight, about 600; manufactured by Wako Pure Chemical Industries, Ltd.), but not subjected to the quaternary ammonium modification step, was provided as Sample M; a filter 7 prepared with a mesh treated with PEI (average molecular weight, about 600; manufactured by Wako Pure Chemical Industries, Ltd.) and ethyl bromide was provided as Sample N; a filter 7 prepared with a mesh treated with (P; manufactured by BASF) and ethyl bromide was provided as Sample O; and a filter 7 prepared with a mesh treated with PEI (LUPASOL (registered trade mark) SK, manufactured by BASF) and ethyl bromide was provided as Sample P.

Samples M to P used for endovascular treatment aiding devices 1 were subjected to evaluation by the human whole blood test. The results are shown in Table 2. As shown in Table 2, no thrombus adhesion (−) was found for Samples M, N, and P, and no thrombus adhesion (−−) was found for Sample O, in the evaluation by the human whole blood test.

Example 8

A mesh was soaked in an aqueous solution of 5% PEI, and heated at 80° C. for 2 hours, thereby covalently binding PEI to the mesh by aminolysis reaction (first coating step). The aqueous solution after the reaction was removed, and the mesh was washed with distilled water. The quaternary ammonium modification step using ethyl bromide was carried out by the same operation as in Mesh C in Example 2, and the second coating step was then carried out. The same reagents as in Example 2 were used except for the antithrombogenic compound.

A filter 7 prepared with a mesh subjected to the first coating step using PEI (average molecular weight, about 600; manufactured by Wako Pure Chemical Industries, Ltd.) was provided as Sample Q; a filter 7 prepared with a mesh subjected to the first coating step using PEI (LUPASOL (registered trade mark) P, manufactured by BASF) was provided as Sample R; and a filter 7 prepared with a mesh subjected to the first coating step using PEI (LUPASOL (registered trade mark) SK, manufactured by BASF) was provided as Sample S.

Samples Q to S used for endovascular treatment aiding devices 1 were subjected to evaluation by the human whole blood test. The results are shown in Table 2. As shown in Table 2, no thrombus adhesion (−) was found in the evaluation by the human whole blood test.

Example 9

A filter 7 prepared with a mesh subjected to the first coating step using PEI (LUPASOL (registered trade mark) P, manufactured by BASF) and then to the quaternary ammonium modification step using ethyl bromide by the same operation as in Mesh C in Example 2, but not subjected to the second coating step, was provided as Sample T. The same reagents as in Example 2 were used except for the antithrombogenic compound.

Sample T used for an endovascular treatment aiding device 1 was subjected to evaluation by the human whole blood test. The results are shown in Table 2. As shown in Table 2, thrombus adhesion (+) was found in the evaluation by the human whole blood test.

Example 10

A filter 7 prepared with a mesh subjected to neither the first coating step using PEI nor the quaternary ammonium modification step, but subjected to the second coating step by the same operation as in the case of Mesh C in Example 2, was provided as Sample U. The same reagents as in Example 2 were used except for the antithrombogenic compound.

Sample U used for an endovascular treatment aiding device 1 was subjected to evaluation by the human whole blood test. The results are shown in Table 2. As shown in Table 2, thrombus adhesion (+) was found in the evaluation by the human whole blood test.

Example 11

The first coating step was carried out by the same operation as in Example 2 except that polyvinyl pyrrolidone (hereinafter referred to as "PVP") (K-90, manufactured by ISP) was used instead of PEI. A filter 7 prepared with a mesh subjected to the quaternary ammonium modification step using ethyl bromide by the same operation as in Mesh C in Example 2 and then to the second coating step was provided as Sample V. The same reagents as in Example 2 were used except for the antithrombogenic compound.

Sample V used for an endovascular treatment aiding device 1 was subjected to evaluation by the human whole blood test. The results are shown in Table 2. As shown in Table 2, thrombus adhesion (+) was found in the evaluation by the human whole blood test.

Example 12

The first coating step was carried out by the same operation as in Example 2 except that benzalkonium chloride (manufactured by Wako Pure Chemical Industries, Ltd.) was used instead of PEI. A filter 7 prepared with a mesh subjected to the quaternary ammonium modification step using ethyl bromide by the same operation as in Mesh C in Example 2 and then to the second coating step was provided as Sample W. The same reagents as in Example 2 were used except for the antithrombogenic compound.

Sample W used for an endovascular treatment aiding device 1 was subjected to evaluation by the human whole blood test. The results are shown in Table 2. As shown in Table 2, thrombus adhesion (+) was found in the evaluation by the human whole blood test.

The endovascular treatment aiding devices were evaluated by the following methods for the antithrombogenicity, the retrieval sheath delivery performance, and catching in a treatment device such as a stent or a guiding catheter during retrieval.

Evaluation 1: Human Whole Blood Test

Filters 7 to which antithrombogenic compounds are bound (Samples A to W), and the same material as the untreated filter 7 (positive control), were cut into test pieces each having an effective surface area of 1.0 cm². The test pieces were soaked in physiological saline at 37° C. for 30 minutes, and then placed in 2-mL microtubes. After adding Heparin Sodium Injection (manufactured by Ajinomoto Pharmaceuticals Co., Ltd.) to fresh human blood to a concentration of 0.5 U/mL, 2 mL of the resulting human blood was added to each microtube, and the microtube was then incubated at 37° C. for 2 hours. Thereafter, the test piece was removed, and rinsed with PBS(−) (manufactured by Nissui Pharmaceutical Co., Ltd.), followed by quantifying the weight of thrombi attached. The thrombus weight was determined by measuring the dry weights of the test piece before the test and the test piece after the rinse, and calculating the difference between these weights. The test was carried out for each of Samples A to W and the positive control in three replicates. In cases where the mean of the relative values of the thrombus weight measured in three replicates, calculated according to Equation (3), was not less than 20%, the sample was judged as having thrombus adhesion, and rated as (+). When the mean was less than 20% or less than 10%, the sample was judged as having no thrombus adhesion, and rated as (−) or (−−), respectively.

$$\text{Relative value of thrombus weight (\%)}=(Bt/Bp)\times 100 \qquad (3)$$

Bt: thrombus weight on a filter 7 to which an antithrombogenic compound is bound Bp: thrombus weight of the positive control Evaluation 2: Comparative Experiments on Catching of Endovascular Treatment Aiding Device During Retrieval To carry out comparative experiments, a guiding catheter for 6 Fr was inserted from Femoral approach using a PCI TRAINER for BEGINNERS (commercially available from Medialpha), which is a two-dimensional blood vessel model, and the distal end of the guiding catheter was placed at the inlet of the portion corresponding to the coronary artery in the two-dimensional blood vessel. In the middle of the coronary artery model, a stent was placed, and the endovascular treatment aiding device of Example 2 was allowed to pass through the inside of the guiding catheter and the stent, to place the filter section in the distal side relative to the stent.

In this state, comparative experiments were carried out in 10 replicates for each experiment to investigate whether or not the endovascular treatment aiding device of Example 2 is caught in the stent or the guiding catheter during its retrieval. The results are shown in Table 1. Table 1 also shows the results of the Comparative Example 1 and the Comparative Example 2.

TABLE 1

| | | Members | | | | Outer diameter of endovascular treatment aiding device | Number of times catching during retrieval | |
|---|---|---|---|---|---|---|---|---|
| | Specification | Shaft | Filter | Antithrombogenic compound | Supporting member | Elastomer | | Stent | Guiding catheter |
| Example 2 | Antithrombogenic endovascular treatment aiding device 1 | Yes (shaft 2) | Yes (filter 7) | Yes | Yes (supporting member 9) | Yes (elastomer member 6) | 1 mm | 0 time/10 times | 0 times/10 times |
| Comparative Example 1 | Antithrombogenic endovascular treatment aiding device 10 | Yes (shaft 2) | Yes (filter 7) | Yes | Yes (supporting member 9) | No | 0.8 mm | 1 time/10 times | 3 times/10 times |
| Comparative Example 2 | Filtrap (registered trademark) FTS-35-18S | Yes | Yes | No | Yes | No | >1.1 mm | Retrieval sheath could not be delivered | |

TABLE 2

| | | Antithrombogenic compound | | Abundance ratio of sulfur atoms (atomic percent) | Abundance ratio of nitrogen atoms (atomic percent) | Surface amount based on anti-factor Xa activity (mIU/cm²) | Thickness of antithrombogenic compound layer (nm) | Carbon numbers of alkyl group | Thrombus adhesion |
|---|---|---|---|---|---|---|---|---|---|
| | Sample | Cationic polymer | Anionic sulfur compound having anticoagulant activity | | | | | | |
| Example 2 | A | PEI | Heparin | 1.4 | 3.4 | 15.7 | 14 | 2 | − |
| | B | PEI | Heparin | 4.0 | 8.3 | 64.2 | 58 | 0 | −− |
| | C | PEI | Heparin | 3.8 | 8.2 | 83.5 | 58 | 2 | −− |
| | D | PEI | Heparin | 3.9 | 8.0 | 88.6 | 61 | 5 | −− |

TABLE 2-continued

| | Sample | Antithrombogenic compound | | Abundance ratio of sulfur atoms (atomic percent) | Abundance ratio of nitrogen atoms (atomic percent) | Surface amount based on anti-factor Xa activity (mIU/cm$^2$) | Thickness of antithrombogenic compound layer (nm) | Carbon numbers of alkyl group | Thrombus adhesion |
| | | Cationic polymer | Anionic sulfur compound having anticoagulant activity | | | | | | |
|---|---|---|---|---|---|---|---|---|---|
| Example 3 | E | PEI | Heparin | 3.3 | 8.0 | Not less than 100 | 510 | 2 | -- |
| | F | PEI | Heparin | 3.5 | 8.2 | Not less than 100 | 415 | 2 | -- |
| Example 4 | G | PEI | Heparin | 4.3 | 8.9 | Not less than 100 | 395 | 2 | -- |
| | H | PEI | Heparin | 3.9 | 9.8 | Not less than 100 | 585 | 2 | -- |
| | I | PEI, PAH | Heparin | 3.4 | 6.5 | 55.4 | 368 | 2 | -- |
| Example 5 | J | PAH | Heparin | 3.2 | 7.3 | 52.3 | 10 | 2 | - |
| | K | PLys | Heparin | 3.2 | 7.1 | 41.5 | 12 | 2 | - |
| Example 6 | L | PEI | Dextran sulfate | 3.6 | 8.2 | — | 60 | 2 | - |
| Example 7 | M | PEI | Heparin | 1.0 | 2.5 | 3.2 | 6 | 0 | - |
| | N | PEI | Heparin | 1.0 | 2.4 | 8.2 | 6 | 2 | - |
| | O | PEI | Heparin | 3.1 | 6.4 | 25.5 | 20 | 2 | -- |
| | P | PEI | Heparin | 1.0 | 2.9 | 8.4 | 11 | 2 | - |
| Example 8 | Q | PEI | Heparin | 1.1 | 2.6 | 8.8 | 9 | 2 | - |
| | R | PEI | Heparin | 1.1 | 3.4 | 10.5 | 10 | 2 | - |
| | S | PEI | Heparin | 1.1 | 3.1 | 10.1 | 10 | 2 | - |
| Example 9 | T | PEI | — | 0.3 | 8.1 | — | 49 | 2 | + |
| Example 10 | U | — | Heparin | 0.8 | — | 0 | <1 | — | + |
| Example 11 | V | PVP | Heparin | 1.2 | 2.5 | 0.5 | 10 | 2 | + |
| Example 12 | W | Benzalkonium chloride | Heparin | 1.5 | 2.9 | 2.3 | 10 | 2 | + |

INDUSTRIAL APPLICABILITY

Our tools can be used as an endovascular treatment aiding device when an endovascular treatment such as balloon angioplasty or stenting using a balloon catheter or a stent is carried out.

The invention claimed is:

1. An endovascular treatment aiding device comprising:
a flexible shaft;
a filter fixed to said shaft such that a closed-end section is formed in a distal side in a longitudinal direction of the shaft, and an opening section is formed in a proximal side in said longitudinal direction, said filter can be opened and closed in an umbrella-like manner;
a supporting member composed of linear members each of which is fixed to an end portion in an opening-section side of said filter and a part of said shaft such that they are connected to each other and the shaft is positioned at a central axis of the filter, said linear members enable closing of said filter by tension applied to the supporting member by proximal retraction of the shaft in said longitudinal direction;
an elastomer member which is a member composed of an elastomer in which a penetrating hole (A) is formed, said elastomer member being arranged in a proximal side relative to the opening section of said filter in said longitudinal direction such that said shaft penetrates said penetrating hole (A), wherein the outer diameter of a terminal distal end face in which said penetrating hole (A) is formed is larger than an outer diameter of the opening-section side of said filter when said filter is closed such that only a proximal portion of the opening-section side of the filter is covered by the terminal distal end face of the elastomer when said filter is closed;
an annular member in which a penetrating hole (C) is formed, said annular member being arranged in the proximal side relative to the opening section of said filter in said longitudinal direction such that said shaft penetrates said penetrating hole (C) in a state allowing movement of said shaft in said longitudinal direction, said annular member having a thick section whose outer diameter is smaller than the outer diameter of the opening-section side of said filter when said filter is closed, and whose outer diameter is larger than an inner diameter of said elastomer member: and
an outer tube in which a penetrating hole (B) is formed, said outer tube being arranged in the proximal side relative to the opening section of said filter in said longitudinal direction such that said shaft penetrates said penetrating hole (B) in a state allowing movement of said shaft in said longitudinal direction;
wherein said elastomer member is fixed in a distal side of said outer tube in said longitudinal direction and the annular member is distal of the terminal distal end face of said elastomer member and the annular member is slidably movable along said shaft, and
wherein, when said outer tube is slid toward the distal side of the shaft in said longitudinal direction, said filter is closed by bundling of said supporting member.

2. The endovascular treatment aiding device according to claim 1, wherein, when said outer tube is slid toward the distal side in said longitudinal direction to close said filter, said endovascular treatment aiding device can have a shape in which said elastomer member covers said thick section, and said thick section is pressed into said penetrating hole (A).

3. The endovascular treatment aiding device according to claim 1, which can be contained in a sheath when said filter is in a closed state.

4. The endovascular treatment aiding device according to claim 3, wherein a ratio of abundance of nitrogen atoms to abundance of total atoms on the surface of said filter as measured by X-ray photoelectron spectroscopy (XPS) is 7.0 to 12.0 atomic percent.

5. The endovascular treatment aiding device according to claim 1, wherein a ratio of abundance of sulfur atoms to abundance of total atoms on the surface of said filter as measured by X-ray photoelectron spectroscopy (XPS) is 3.0 to 6.0 atomic percent.

6. The endovascular treatment aiding device according to claim 1, wherein said filter is formed with polyester.

7. The endovascular treatment aiding device according to claim 1, wherein the filter comprises a flexible ring having elastic restoring force and the ring freely bends during opening and closing of the filter in an umbrella-like manner.

8. The endovascular treatment aiding device according to claim 1, wherein a cationic polymer containing, as constituent monomers, at least one compound selected from the group consisting of alkyleneimine, vinylamine, allylamine, lysine, protamine, and diallyldimeth-ylammonium chloride is covalently bound to said filter, and an anionic sulfur compound having anticoagulant activity is bound to said filter and/or said cationic polymer.

9. The endovascular treatment aiding device according to claim 8, wherein said anionic sulfur compound having anticoagulant activity is at least one selected from the group consisting of heparin and heparin derivatives.

10. The endovascular treatment aiding device according to claim 8, wherein a surface amount of said anionic sulfur compound having anticoagulant activity on said filter after soaking in physiological saline at 37° C. for 30 minutes as measured based on the anti-factor Xa activity is not less than 30 mIU/cm$^2$.

11. The endovascular treatment aiding device according to claim 8, wherein said cationic polymer and said anionic sulfur compound having anticoagulant activity form an antithrombogenic compound layer with a thickness of 1 to 600 nm on the surface of said filter.

* * * * *

UNITED STATES PATENT AND TRADEMARK OFFICE
CERTIFICATE OF CORRECTION

PATENT NO. : 10,660,738 B2
APPLICATION NO. : 15/306505
DATED : May 26, 2020
INVENTOR(S) : Inoue et al.

Page 1 of 1

It is certified that error appears in the above-identified patent and that said Letters Patent is hereby corrected as shown below:

In the Claims

In Column 31
At Line 2, please change "claim 3" to --claim 1--.

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*